US012697103B2

(12) United States Patent
Lyutakov et al.

(10) Patent No.: US 12,697,103 B2
(45) Date of Patent: Aug. 4, 2026

(54) SWALLOWABLE CAPSULE FOR OBTAINING A FLUID SAMPLE FROM THE GI TRACT OF A SUBJECT

(71) Applicant: Capsibo AD, Sofia (BG)

(72) Inventors: Ivan Aleksandrov Lyutakov, Sofia (BG); Angel Ventsislavov Petkov, Pazardzhik (BG); Simeon Yankov Yanchev, Sofia (BG)

(73) Assignee: Capsibo AD, Sofia (BG)

( * ) Notice: Subject to any disclaimer, the term of this patent is extended or adjusted under 35 U.S.C. 154(b) by 586 days.

(21) Appl. No.: 18/106,067

(22) Filed: Feb. 6, 2023

(65) Prior Publication Data

US 2023/0263510 A1 Aug. 24, 2023

(30) Foreign Application Priority Data

Feb. 7, 2022 (EP) ..................................... 22155384

(51) Int. Cl.
*A61B 10/00* (2006.01)

(52) U.S. Cl.
CPC .. *A61B 10/0045* (2013.01); *A61B 2010/0061* (2013.01); *A61B 2562/162* (2013.01)

(58) Field of Classification Search
None
See application file for complete search history.

(56) References Cited

U.S. PATENT DOCUMENTS

| | | | |
|---|---|---|---|
| 5,316,015 A * | 5/1994 | Sinaiko | A61B 10/02 600/593 |
| 2004/0097834 A1* | 5/2004 | Stoltz | A61B 10/0045 600/573 |
| 2017/0252017 A1 | 9/2017 | Wrigglesworth et al. | |
| 2019/0223846 A1* | 7/2019 | Kerkhof | A61B 10/0045 |

FOREIGN PATENT DOCUMENTS

WO 2020214689 A1 10/2020

OTHER PUBLICATIONS

European Search Report 22155384.5 dated Jul. 12, 2022.

* cited by examiner

*Primary Examiner* — Aurelie H Tu
(74) *Attorney, Agent, or Firm* — Carter, DeLuca & Farrell LLP

(57) ABSTRACT

A swallowable capsule for obtaining fluid samples from the gastrointestinal (GI) tract of a subject. The capsule comprises an outer shell having an inlet port that allows a fluid sample to enter into the interior space of the capsule. A piston is arranged in the interior space and can be moved via a pressure generating device to exert pressure on one side of the piston to propel the piston from an open position, in which fluid can enter the capsule from outside to a closed position, in which entrance of fluid from outside the capsule is prevented. The piston has at least one seal portion that closes the shell opening in the closed position. A control unit is configured to control the pressure generating device so as to move the piston in a forward direction from the open position to the closed position.

13 Claims, 12 Drawing Sheets

SWALLOWABLE CAPSULE FOR OBTAINING A FLUID SAMPLE FROM THE GI TRACT OF A SUBJECT

The present disclosure relates to ingestible devices configured to obtain fluid samples from the GI tract of a subject.

The devices can be designed to allow analysis/assaying of the sample while the device is still present in the subject, and/or can be designed for the sample to be analyzed/assayed after the device exits the subject. Further, the device allows for control over the amount of sample that is taken in by the device.

BACKGROUND

It is known in the field of medicine that the gastrointestinal (GI) tract, and in particular its microbiological content, are essential to the health of the entire body. In particular, the contents in the GI tract may provide information regarding certain diseases or disorders. An analysis of fluid samples from the GI tract thus makes it possible to get a direct insight into the metabolism of an individual and to determine the causes of certain diseases or disorders.

There are already different types of ingestible devices that can obtain a sample when in the GI tract of a subject. Prior art devices are normally comprised of a swallowable capsule having an outer shell with an inlet port that allows a fluid sample to enter into the swallowable capsule. Inside the shell there is a sampling chamber which serves to hold and retain samples obtained from the GI tract.

For example, an ingestible device configured to obtain fluid samples from the GI tract of a subject is disclosed in WO 2018/035394 A1. Another ingestible device for collecting samples from the GI tract of an individual is disclosed in WO 2018/035394 A1.

The aforementioned ingestible devices comprise a multi-stage valve system configured to open or close an inlet port provided in the outer shell of the device, thereby either enabling fluid communication or blocking fluid communication between an exterior of the ingestible device and an interior of the ingestible device. The multi-stage valve system proposed in the aforementioned patent applications is driven by an electromechanical drive unit which is quite large and fairly complex. Hence, the ingestible device itself is fairly large, too, which is disadvantageous for the use of the device.

It is therefore an object of the present invention to provide a swallowable capsule for obtaining a fluid sample from the GI tract of a subject having smaller dimensions and a less complex closure mechanism for opening or closing an inlet port provided in the outer shell of the device.

SUMMARY

In order to solve said problem, the present invention proposes a swallowable capsule configured to obtain fluid samples from the gastrointestinal (GI) tract of a subject comprising:

an outer shell surrounding an interior space;
the outer shell having at least one shell opening serving as an inlet port that allows a fluid sample to enter into the swallowable capsule;
a sampling chamber which may hold one or more samples obtained from the GI tract;
a piston which is moveable in the interior space;
a gas drive unit comprising a pressure generating device that builds up pressure on one side of the piston to propel the piston in the interior space in a forward direction at least from an open position allowing fluid from outside the swallowable capsule to enter into the capsule to a closed position, in which fluid exterior to the swallowable capsule is prevented from entering into the sampling chamber;
the piston comprising at least one seal portion that closes the shell opening in the closed position of the piston; and
a control unit configured to control the pressure generating device so as to move the piston in the forward direction from the open position to the closed position.

In some embodiments, the piston may be equipped with:
a first seal portion that closes the at least one shell opening in a first position (which is a closed position) of the piston thereby preventing fluid exterior to the swallowable capsule from entering into the capsule;
at least one piston opening that may be arranged in line with the shell opening in a second position (which is an open position) of the piston thereby allowing fluid exterior to the swallowable capsule to enter into the capsule;
a second seal portion that closes the at least one shell opening in a third position (which is a closed position) of the piston thereby preventing fluid exterior to the swallowable from entering into the capsule.

In such embodiments, the swallowable capsule preferably comprises a microprocessor that is configured to control the gas drive unit so as to propel the piston in the forward direction from the first position to the second position and from the second position to the third position.

In some embodiments, the piston may comprise just one seal portion that closes the shell opening in a closed position of the piston. In an initial state, the piston preferably rests in an open position allowing fluid exterior to the swallowable capsule to enter into the sampling chamber. After a fluid sample has been collected from the GI tract, the piston is moved into the closed position thereby blocking a passageway between the outer shell openings and the sampling chamber. In such embodiments, the piston does not necessarily require a piston opening and/or a second seal portion as mentioned above. The control unit is preferably configured to control the pressure generating device so as to move the piston in the forward direction at least from the open position to the closed position.

In some embodiments, the shell opening(s) may be closed with a soluble seal which dissolves after a given period of time in the gastrointestinal (GI) tract of the subject thereby unblocking the shell opening(s) and allowing fluid from outside the swallowable capsule to enter into the capsule. In this case, the control unit will slide the piston into the closed position after the soluble seal has been absorbed and a fluid sample has entered into the sampling chamber.

As regards actuation of the piston, the movement of the piston may simply be time-controlled. In this case, the piston may be actuated at a fixed period of time after the capsule has been swallowed. In another embodiment, the piston is actuated in response to detecting that a fluid sample has entered into the sampling chamber. To this end, the swallowable capsule may comprise a fluid detector or any other kind of sensor which is apt to indicate that a fluid sample has entered into the sampling chamber.

The soluble seal may be provided to close the shell opening only, or to cover part of the swallowable capsule or the entire capsule.

The soluble seal may be made of an enteric material to prevent or minimize dissolution in the stomach, allowing it dissolve only in the small intestine. Suitable materials may comprise, but are not limited to plant-derived HPMC or HPMCP.

The aforementioned moveable piston divides the interior space into a high-pressure side, on which the pressure generating device builds up pressure to propel the piston in the forward direction, and a low-pressure side.

In some embodiments, the piston has a main body and an extension extending away from the main body in a forward direction. The extension may comprise one or more of the following features: a seal portion, at least one piston opening, a second seal portion.

The aforementioned extension is preferably arranged on the low-pressure side or front side, respectively, of the piston.

The piston may comprise a disc-shaped main body element, the extension extending away from the disc-shaped main body element in a forward direction.

In some embodiments, the extension has the shape of a hollow cylinder. In other embodiments, the extension comprises one or several arms which extend in the forward direction on the low-pressure side of the piston.

The outer shell may have an interior wall along which the piston slides. In some embodiments, the piston extends flush against and parallel to the interior wall of the shell.

The aforementioned sampling chamber preferably has one or more chamber openings that allow a fluid sample to enter into the sampling chamber.

In some embodiments, the chamber openings point in a lateral direction, i. e. transversely to the forward direction.

The at least one shell opening and the chamber opening may be aligned on top of each other. In such an embodiment, by bringing the piston opening(s) in line with the at least one shell opening and the chamber opening(s), fluid exterior to the swallowable capsule may enter through the shell opening into the capsule, pass the piston opening and flow through the chamber opening into the sampling chamber.

According to a general concept, the piston is configured to open or close the at least one shell opening as well as the chamber opening(s) at the same time, when in the first, second or third position.

In a preferred embodiment, the sampling chamber is arranged on a low-pressure side of the piston.

In some embodiments, the extension of the piston travels in a space between an interior wall of the shell and an exterior wall of the sampling chamber. In such an embodiment, the interior wall of the shell and the exterior wall of the sampling chamber are preferably parallel with each other.

In some embodiments, the outer shell has an outlet port which allows gas from the interior space on the low-pressure side of the piston to exit the capsule to the exterior. The outlet port may be closed with a physical barrier which prevents fluid from the exterior from entering into the capsule. For example, the barrier may comprise a membrane or a sponge-like material.

The aforementioned pressure generating device may comprise a gas-generating cell that generates gas in a chemical process and thus causes an internal pressure to drive the piston. Alternatively, the pressure generating device may comprise a pressure capsule which is filled with a pressurized gas (e.g. air) which may be released through a valve. The pressure generating device may also comprise one or more tubes, valves, electronics, etc.

According to one aspect of the invention, the swallowable capsule further comprises a microcontroller configured to control the pressure-generating device, in particular to control the generation of gas and/or to manipulate a valve so as to build up pressure in a controlled manner.

The swallowable capsule according to the present invention may further comprise a locking means configured to hold the piston in place in at least the second, open position in which a fluid sample from the GI tract may be collected. The locking means may comprise a snap-in locking mechanism which releasably holds the piston in position. The snap-in locking mechanism may comprise a latch and a notch which engage when the piston is in the desired position. But basically, any suitable locking mechanisms may be used to hold the piston in the desired position.

In other embodiments, the sampling chamber may include an absorbent material and a preservative, such as an analyte preservative.

In some embodiments, the sampling chamber may be an integral part of the swallowable capsule. The shell of the swallowable capsule may be made of metal, plastics or any other synthetic material which is apt to withstand the atmosphere within the GI tract of an individual.

The location of the swallowable capsule within the GI tract of an individual may be detected in a number of different ways. For example, light emitting diodes may be used to emit light, and sensors may be positioned along the capsule to determine whether the capsule is in the stomach, small intestine, or large intestine. Methods for determining the location of a swallowable capsule are described in greater detail in PCT Application No. PCT/US 15/52500. Besides the tracking of the capsule by means of on-board sensors, the location of the swallowable capsule within the GI tract of an individual may also be recognized from outside the body, for example via a radio frequency identification (RFID) tag included in the capsule, an ultrasonic device or any other suitable medical apparatus used to gain insight into the interior of a body.

The swallowable capsule is preferably configured to collect a fluid sample in response to determining that the capsule has reached a predetermined location within the GI tract. For example, a microcontroller on board the swallowable capsule may be configured to open the at least one shell opening when the swallowable capsule is within the small intestine, thereby obtaining a sample from within the small intestine.

In other embodiments, actuation of the piston in a forward direction may be time-triggered. It is well-known that substances travel for approx. 6-8 hours through the small intestine, which gives a pretty wide window to take the sample based solely on the time after capsule intake. In a time-triggered embodiment, the control unit may be configured to move the piston once a preset period of time has elapsed after the capsule has been swallowed or a timer has started.

The valve system (piston) for opening or closing the inlet port of the shell may be activated automatically by the on-board microcontroller in response to determining that the capsule has reached a predetermined location within the GI tract or a preset given period of time has elapsed, or the valve system may be activated by a person via a mobile app or a device which is configured to communicate with the swallowable capsule via RF, Bluetooth, a magnetic field or any other well-known wireless technology.

Further, some embodiments of the swallowable capsule may comprise a position sensor for detecting the position of the piston. Any type of known proximity sensor may be used to this end. A special embodiment of a position sensor may comprise one or more, in particular two, springs extending between the piston and a contact surface providing an electrical contact. One end of the spring(s) is preferably attached to the piston, the other end is preferably free and moveable between a first position in which it is in contact with the electrical contact, and a second position in which it is lift off from the electrical contact.

In an initial state of the piston, the springs are compressed between the piston and the contact surface. When the piston slides forward, the spring(s) extend until they reach their complete length. At a certain point, at least one of the springs will lift from the contact surface, thereby indicating that the piston has reached a certain position. Several springs may be arranged in a parallel relationship. One of the springs may be shorter than another one of the in order to be able to detect different positions of the piston.

The piston may be made of plastics, rubber or metal.

BRIEF DESCRIPTION OF THE DRAWINGS

The drawings annexed hereto show a number of exemplary embodiments. In the drawings:

FIG. 2a-2c are sectional views of the swallowable capsule of FIG. 1 illustrating a valve system or closure mechanism, respectively, including a piston for opening and closing the shell openings, wherein FIG. 2a shows the piston in a first position, FIG. 2b shows the piston in a second position and FIG. 2c shows the piston in a third position;

FIG. 5a-5c are sectional views of a swallowable capsule according to a second embodiment of the present invention having a modified piston and a soluble seal covering the outer shell, wherein FIG. 5a shows the piston in a first, open position with the seal fully intact, FIG. 5b shows the piston in the first, open position after the seal has dissolved, and FIG. 5c shows the piston in a second, closed position.

Figure 1:
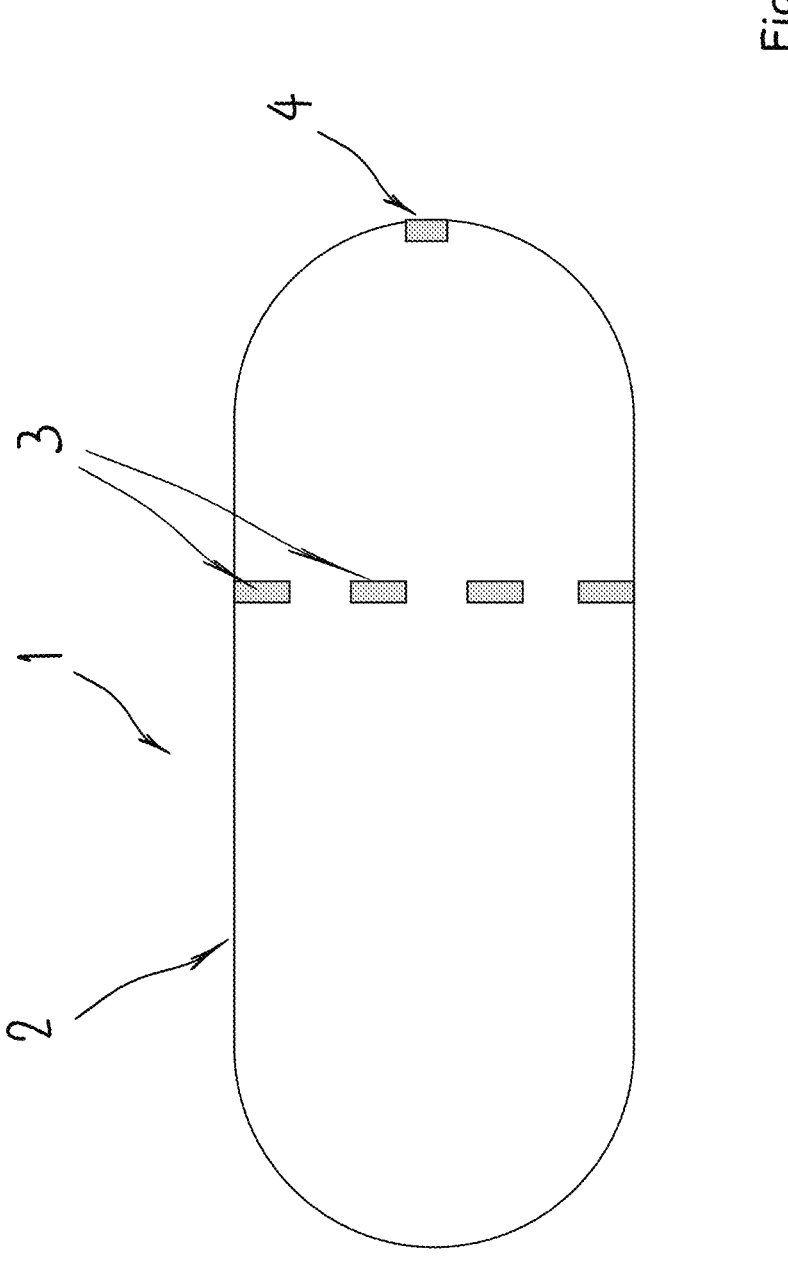
FIG. 1 is an outside view of an illustrative first embodiment of a swallowable capsule with multiple shell openings.

What is proposed is a swallowable capsule (1) configured to obtain fluid samples from the gastrointestinal (GI) tract of a subject comprising: an outer shell (2) surrounding an interior space (17); the outer shell 5 (2) having at least one shell opening (3) serving as an inlet port that allows a fluid sample to enter into the swallowable capsule (1); a sampling chamber (21) which may hold one or more samples obtained from the GI tract; a piston (5) which is moveable in the interior space (17); a gas drive unit comprising a pressure generating device (10) that may 10 build up pressure on one side of the piston (5) to propel the piston (5) in the interior space (17); the piston (5) having: a first seal portion (8) that closes the at least one shell opening (3) in a first position of the piston (5) thereby preventing fluid exterior to the swallowable capsule (1) from entering into the capsule (1); at least one piston opening (9) that may be arranged flush with the shell opening (3) 15 in a second position of the piston (5) thereby allowing fluid exterior to the swallowable capsule (1) to enter into the capsule (1); a second seal portion (7) that closes the at least one shell opening (3) in a third position of the piston (5) thereby preventing fluid exterior to the swallowable capsule (1) from entering into the capsule (1); a microprocessor (12) configured to control the gas drive unit so as to 20 consecutively propel the piston (5) in a forward direction (A) from the first position to the second position and to the third position. The gas drive unit eliminates the need for complex and space-occupying mechanics and is also very energy efficient.

FIG. 1 illustrates an example swallowable capsule 1 having an outer shell 2 with a first end (on the right-hand side), a second end (on the left-hand side), and a wall extending longitudinally from the first end to the second end. There are multiple shell openings 3 in the shell 2 which allow obtaining a sample from the GI tract of an individual, for instance when the swallowable capsule 1 is within the small intestine. Thereby, the shell openings 3 serve as an inlet port that allows the fluid sample to enter into the swallowable capsule 1.

For illustrative purposes, the shell openings 3 located in the wall are oriented radially and point in a lateral direction. However, in some embodiments, the exact location and orientation of the shell openings 3 may be different from that shown in FIG. 1. For example, at least one shell opening 4 may be oriented in a longitudinal direction while other shell openings 3 point in a lateral direction. During transit through the GI Tract, natural contractions within the small intestine may apply pressure perpendicularly to different portions of the shell 2 of the swallowable capsule 1, which may force solids or fluids into the shell openings 3.

The overall shape of the swallowable capsule 1 may be similar to an elongated pill or capsule. This may make the swallowable capsule 1 easy to consume, and allow it to travel easily through the GI tract. As used herein, the term "gastrointestinal tract" or "GI tract" refers to all portions of an organ system responsible for consuming and digesting foodstuffs, absorbing nutrients, and expelling waste. This includes orifices and organs such as the mouth, throat, esophagus, stomach, small intestine, large intestine, rectum, anus, and the like, as well as the various passageways and sphincters connecting the aforementioned parts.

Figure 2A:
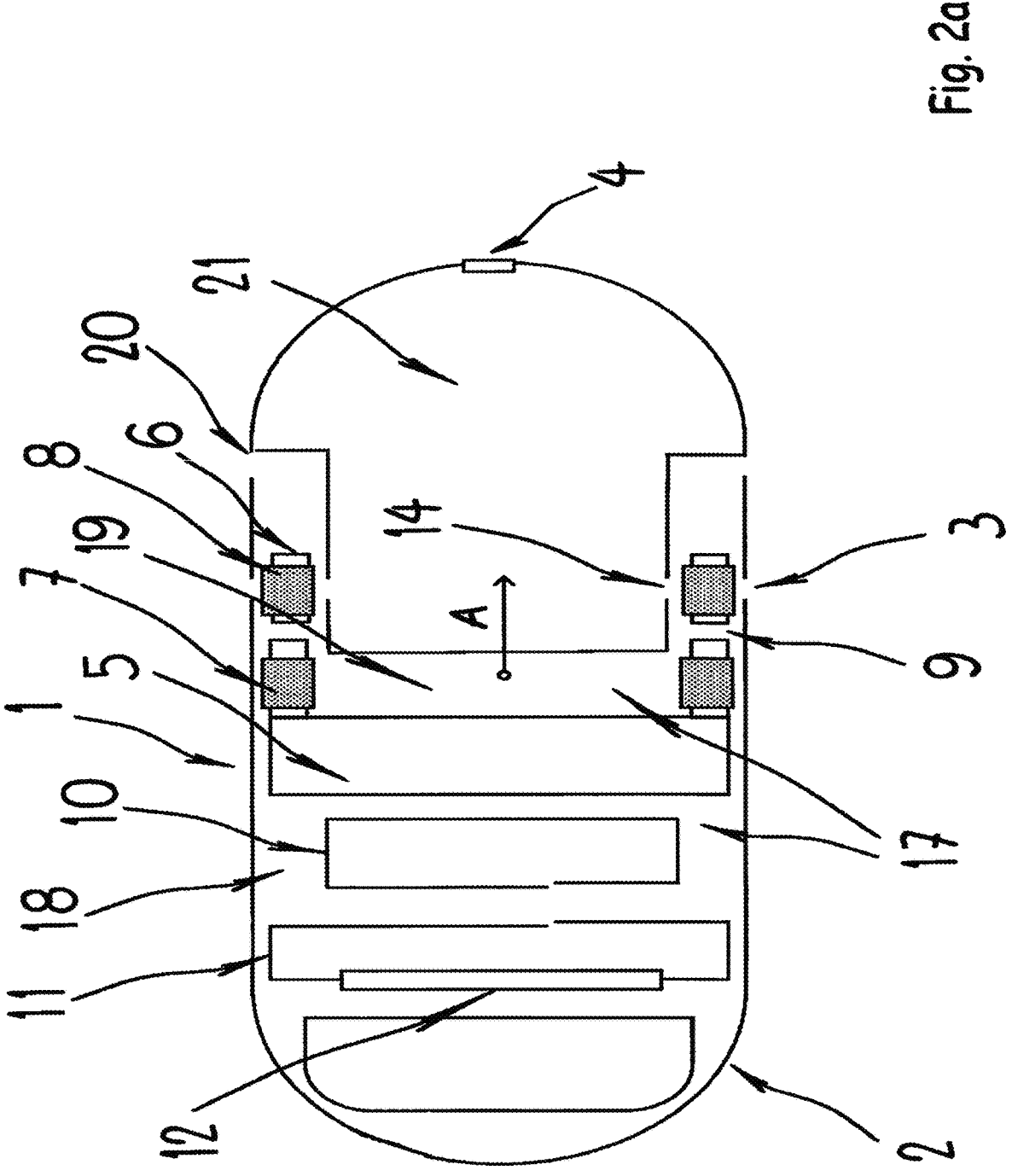
Figure 2B:
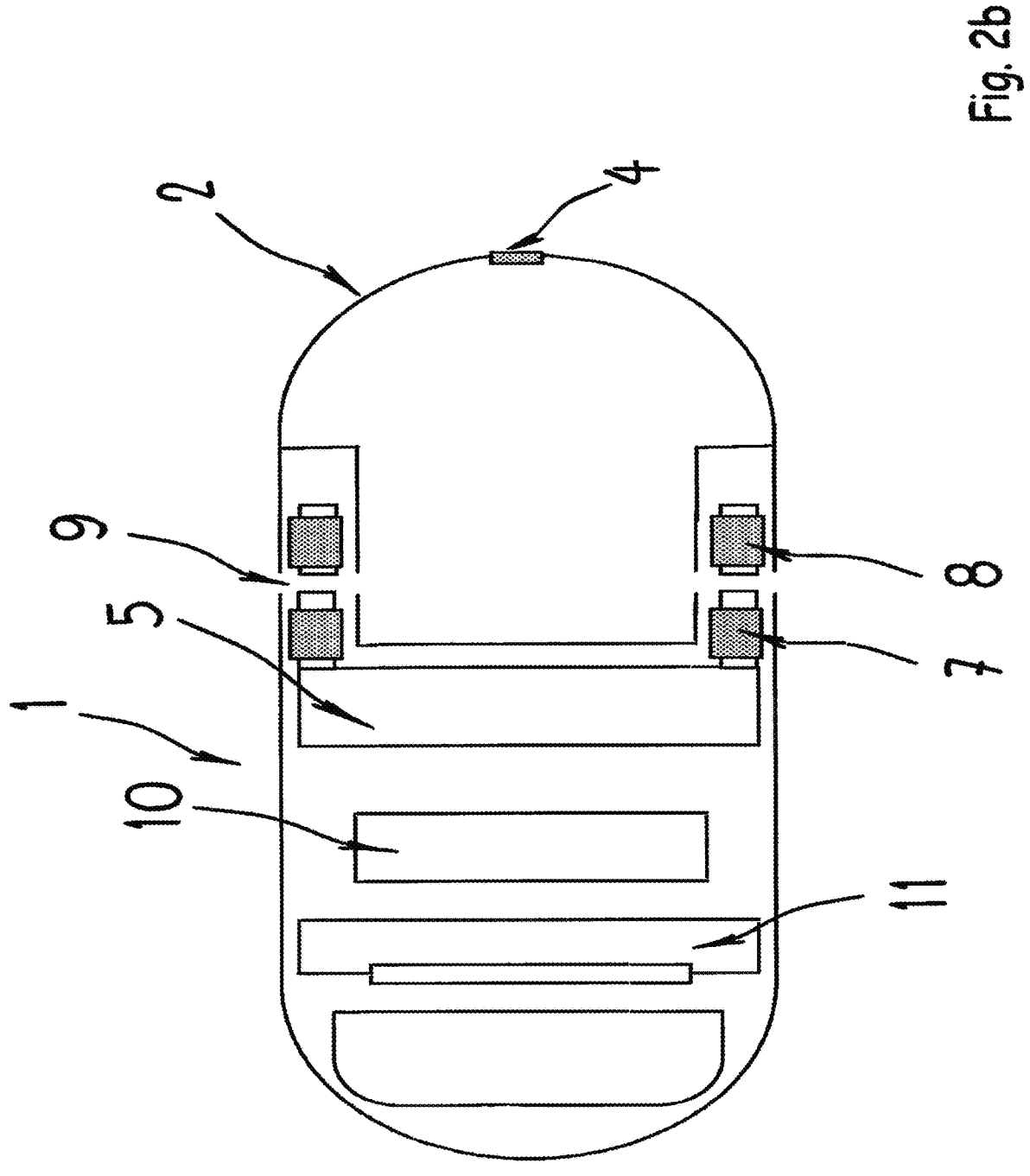
Figure 2C:
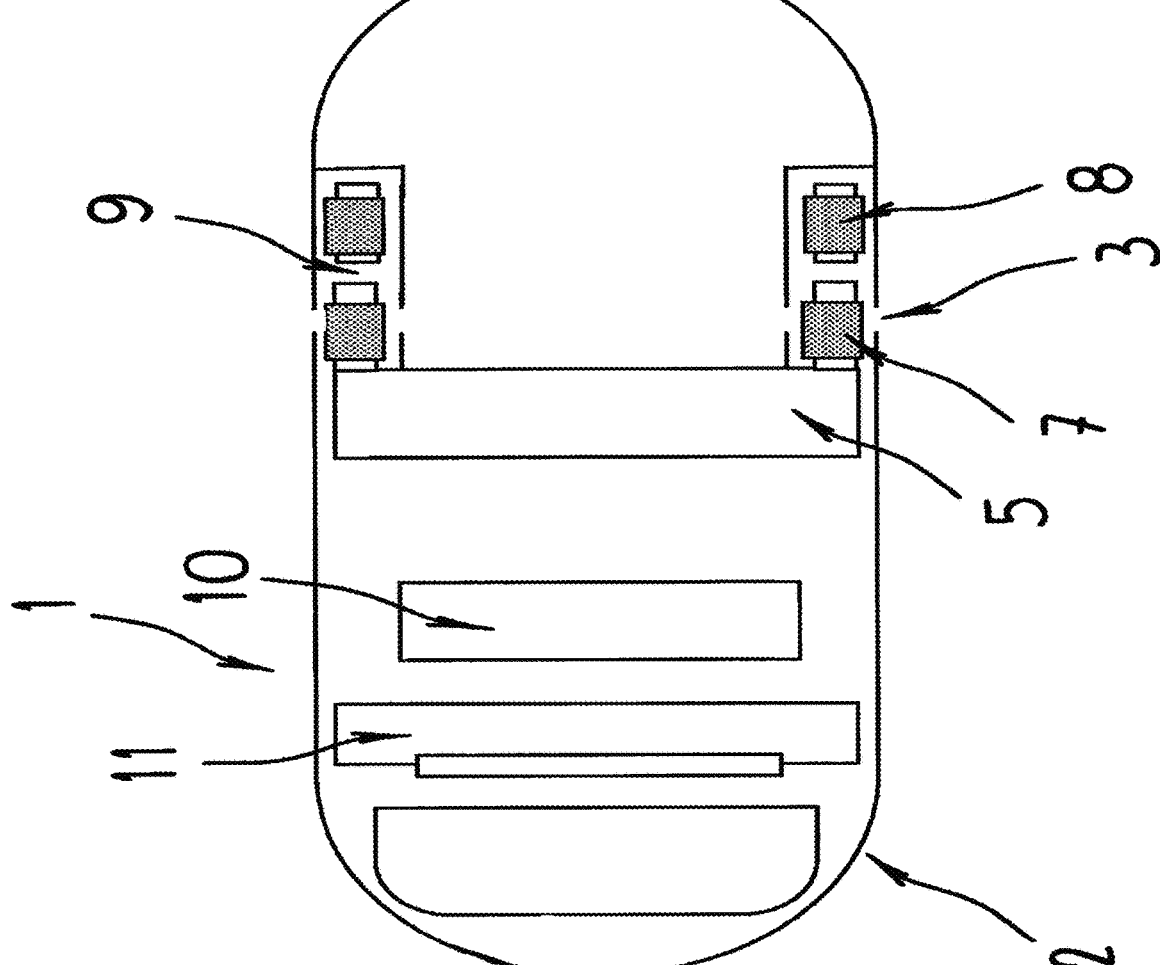

As shown in FIGS. 2a-2c, the outer shell 2 surrounds an interior space 17 which houses various components of the swallowable capsule 1. One of them is a sampling chamber 21 which may hold one or more samples obtained from the GI tract. The swallowable capsule 1 further comprises a closure mechanism including a piston 5 configured to open or close the shell openings 3 provided in the outer shell 2, thereby either enabling fluid communication or blocking fluid communication between an exterior of the swallowable capsule 1 and the interior of the swallowable capsule 1. The piston 5 is moveable in the interior space 17 in a forward direction A.

In FIG. 2a, the piston 5 is depicted as having a first seal portion 8 that is flush with the shell openings 3 so that it prevents fluid exterior to swallowable capsule 1 from entering swallowable capsule 1. As described in more detail below with reference to FIGS. 2b and 2c, the piston 5 can change position so that it allows fluid exterior to swallowable capsule 1 to enter into the capsule 1 and to reseal the shell openings 3 thereafter.

As shown in FIGS. 2a-2c, swallowable capsule 1 comprises a gas drive unit including a pressure generating device 10 which is arranged to build up pressure on one side of the piston 5 so as to propel the piston 5 in the interior space 17 in a forward direction A. Correspondingly, that part of the interior space 17 (here on the left-hand side) where there is a higher pressure is referred to as the "high-pressure side" 18. The other side of the piston 5 (here the right-hand side) is referred to as the "low-pressure side" 19.

In FIG. 2a, the piston 5 is flush against, and parallel with, an inner wall of the shell 2 and covers shell openings 3 to prevent fluid exterior to swallowable capsule 1 (e.g., fluid in the GI tract) from entering the interior of swallowable capsule 1. In the embodiment shown here, piston 5 comprises a first seal portion 8 that closes the shell openings 3 in a first position of the piston 5 as shown in FIG. 2a, one or more piston openings 9 that may be arranged in line with the shell openings 3 in a second position of the piston 5 thereby allowing fluid exterior to the swallowable capsule 1 to enter into the capsule 1, and a second seal portion 7 that recloses the shell openings 3 in a third position of the piston 5 thereby preventing fluid exterior to the swallowable capsule 1 from entering into the capsule 1.

FIG. 2b shows the swallowable capsule 1 with the piston in the second, open position allowing fluid exterior to the swallowable capsule 1 to enter into the capsule 1 and into the sampling chamber 21. FIG. 2c shows the swallowable capsule 1 with the piston in the third, closed position preventing fluid exterior to the swallowable capsule 1 from entering into the capsule 1.

In the embodiment illustrated in the figures, the piston 5 comprises a disc-shaped body element and an extension 6 extending away from the disc-shaped body element in the forward direction A. The extension 6 is located on the low-pressure side 19 of piston 5. In the embodiment of FIGS. 2a-2c, the extension 6 is formed as a hollow cylinder, however, the shape the of the piston 5 may be different from that shown in FIGS. 2a-2c. For example, the piston 5 may comprise one or several arms which extend in the forward direction A on the low-pressure side 19.

In the present embodiment, the extension 6 comprises several first seal portions 8 and several piston openings 9. In addition, the extension 6 features several second seal portions 7.

The aforementioned sampling chamber 21 is provided with several chamber openings 14 that allow a fluid sample to enter into the sampling chamber 21. Said chamber openings 14 point in a lateral direction, i. e. transversely to the forward direction A. Also, the shell openings 3 are oriented in the lateral direction.

As shown in FIGS. 2a-2c, the shell openings 3 and the chamber openings 14 are aligned on top of each other so that, by bringing the piston openings 9 in line with the shell openings 3 and the chamber openings 14, fluid exterior to the swallowable capsule 1 may enter through the shell openings 3 into the capsule 1, pass the piston openings 9 and flow through the chamber openings 14 into the sampling chamber 21.

According to a general concept of this embodiment, the piston 5 is configured to open or close the shell openings 3 as well as the chamber openings 14 at the same time, when it is moved from the first to the second position and finally to the third position. To this end, the extension 6 of the piston 5 is configured to travel in a space between an interior wall of the shell 2 and an exterior wall of the sampling chamber 21. The interior wall of the shell 2 and the exterior wall of the sampling chamber 21 are parallel.

The exemplary swallowable capsule 1 also includes an outlet port 20, which is connected to the volume within shell 2 of the swallowable capsule 1. As can be seen in FIGS. 2a-2c, the volume of interior space 17 on the right-hand side of extension 6 is compressed when the piston 5 moves to the right. The outlet port 20 may provide a path for the gas to exit the swallowable capsule 1 and be released into the environment surrounding the swallowable capsule 1, thereby preventing pressure from building up on the low-pressure side 19 of the piston 5. In another embodiment, where the space on the right-hand side of the projection is large enough, the swallowable capsule 1 does not include an outlet port 20, and the gas stays inside the volume of the swallowable capsule 1.

In some embodiments, the outlet port 20 may contain a gas permeable membrane, a one-way valve, a hydrophobic channel, a sponge-like material or some other mechanism to avoid unwanted material, (e.g., fluids and solid particulates from within the GI tract), from entering the swallowable capsule 1 through the outlet port 20.

As mentioned before already, the swallowable capsule 1 comprises a pressure generating device 10 that is configured to increase pressure on the high-pressure side of the piston so as to propel the piston 5 in the forward direction A. The pressure generating device 10 may comprise a gas-generating cell that generates gas in a chemical process and thus causes an internal pressure to build up within the shell 2. Alternatively, the pressure generating device 10 may comprise a pressure capsule which is filled with a pressurized gas (e.g. air) which may be released through a valve under control of an on-board microcontroller or control unit 12. Further, a PCB 11 is provided which may comprise electric circuits or devices for controlling the movement of the piston 5 or other components of the capsule, or for storing or evaluating data.

In one implementation, the gas-generating cell may be a hydrogen-generating cell, such as but not limited to a Varta® Hydrogen gas-generating cell. In another implementation, one or more other gas-generating cells that generate an inert gas that is harmless to the human body may be used.

In some implementations, the gas-generating cell may include or be connected to a separate channel or valve of the swallowable 1 capsule device such that gas may be released through the channel or valve to create a motion to alter the position of the swallowable capsule 1 within the GI tract. Such gas release can also be used to position the swallowable capsule 1 relative to the intestinal lining.

In some embodiments, a feedback control circuit (e.g., a feedback resistor, etc.) may be added to send feedback from the pressure generating device 10 to the microcontroller 12 such that when the internal pressure reaches a threshold level, the microcontroller may control the pressure generating device 10 stop increasing pressure, or to activate a safety mechanism (e.g., a release valve, etc.). For example, an internal pressure sensor may be used to measure the internal pressure within the ingestible device and generate feedback to the microcontroller 12.

In the embodiments as illustrated in the FIGS. 2a-2c, the microcontroller 12 is configured to control the gas drive unit so as to consecutively propel the piston 5 in a forward direction A from the first position to the second position and to the third position. The beginning of the movement of the piston 5, its traveling speed and in particular the period it rests in the second, open position are controlled by the microcontroller 12. The corresponding settings can be adjusted as desired. For example, the microcontroller 12 on board the swallowable capsule 1 may be configured to propel the piston 5 and to open the shell openings 3 in response to determining that the capsule has reached a predetermined location within the GI tract. Instead of controlling the piston 5 based on information relating to the location of the capsule within the GI tract, the movement of the piston 5 may simply be time-controlled. The piston 5 stays in the second, open position for a predetermined period of time before it is propelled to the third, closed position.

In some embodiments the sampling chamber 21 is subdivided into sub-chambers, each of which may be separated by a series of one or more valves or interlocks. For example, sub-chambers may be used to retain multiple samples. In some embodiments, the sub-chambers of additional chambers are connected to other chambers within the ingestible device 1, or other openings provided in the shell 2 of the capsule 1. This may allow new samples to be acquired while older samples of interest are still stored within the capsule 1.

In some embodiments, the swallowable capsule 1 is equipped with sensors to detect the properties of a sample contained in the sampling chamber 21, or the results of an assay technique applied to the sample. In some embodiments, the swallowable capsule 1 is configured to obtain and retain a sample within the sampling chamber 21, which may be retrieved and analyzed at a later time.

Figure 3:
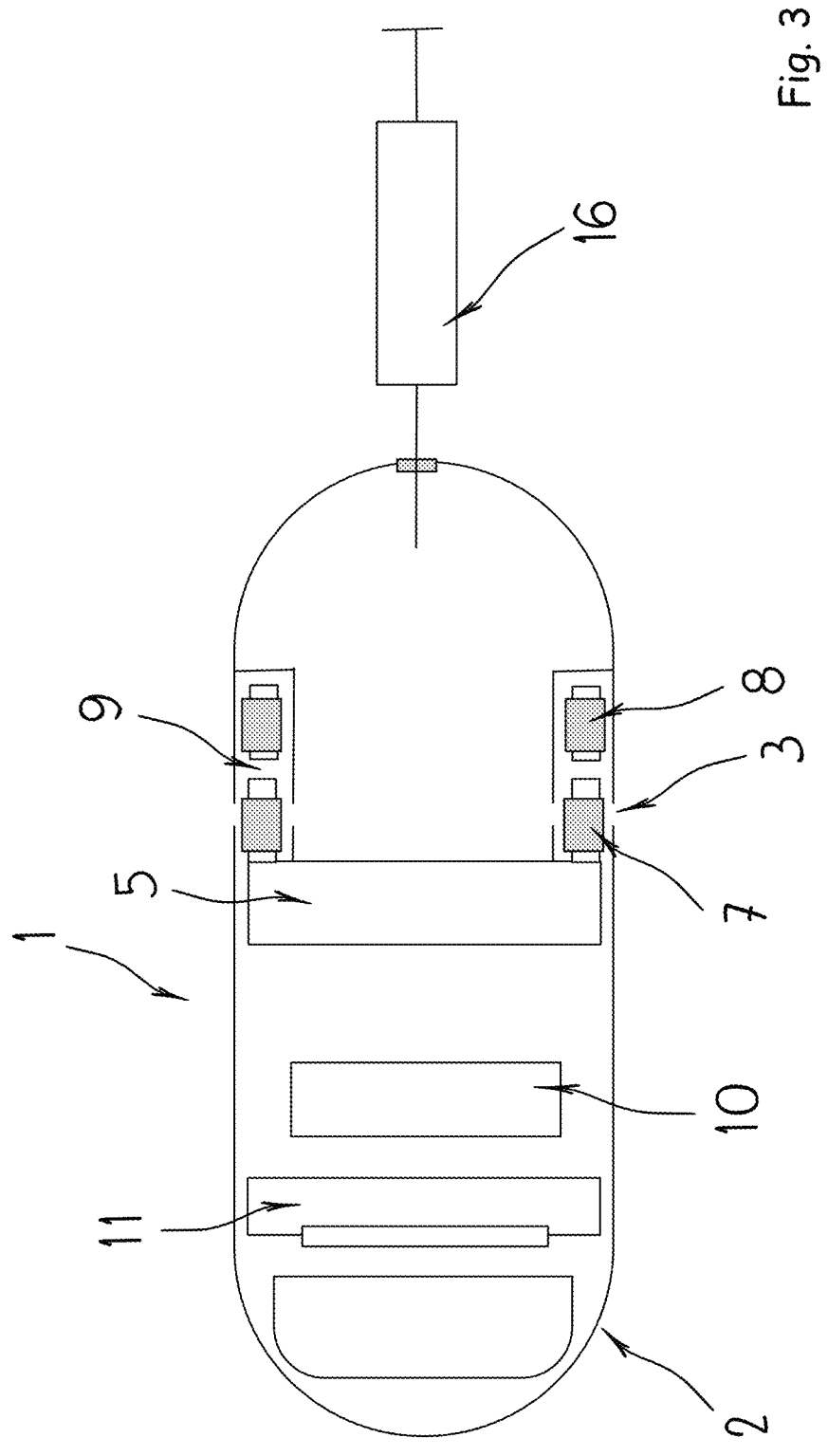
FIG. 3 is a sectional view of the swallowable capsule of FIG. 1 in state where a sample is extracted from a sampling chamber by means of a syringe.

FIG. 3 is a sectional view of the swallowable capsule of FIG. 1 in state where a sample is extracted from a sampling chamber 21 by means of a syringe 16. To this end, the swallowable capsule 1 comprises a window 4 provided in the outer shell 2 which is closed with a seal which can be pierced with a syringe to extract a portion of the fluid sample.

Figure 4:
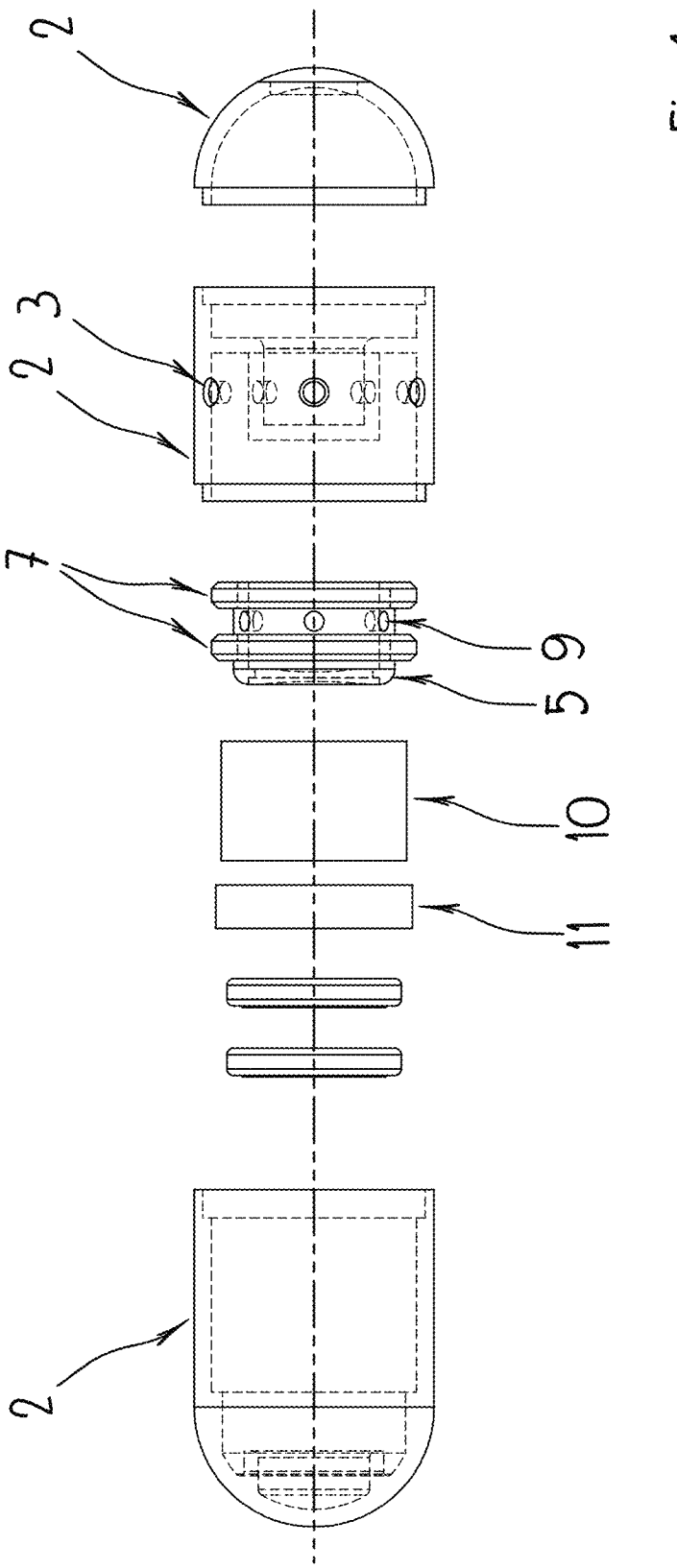
FIG. 4 is an exploded view of the swallowable capsule of FIG. 1.

FIG. 4 shows the swallowable capsule of FIG. 1 in an exploded view.

Figure 5A:
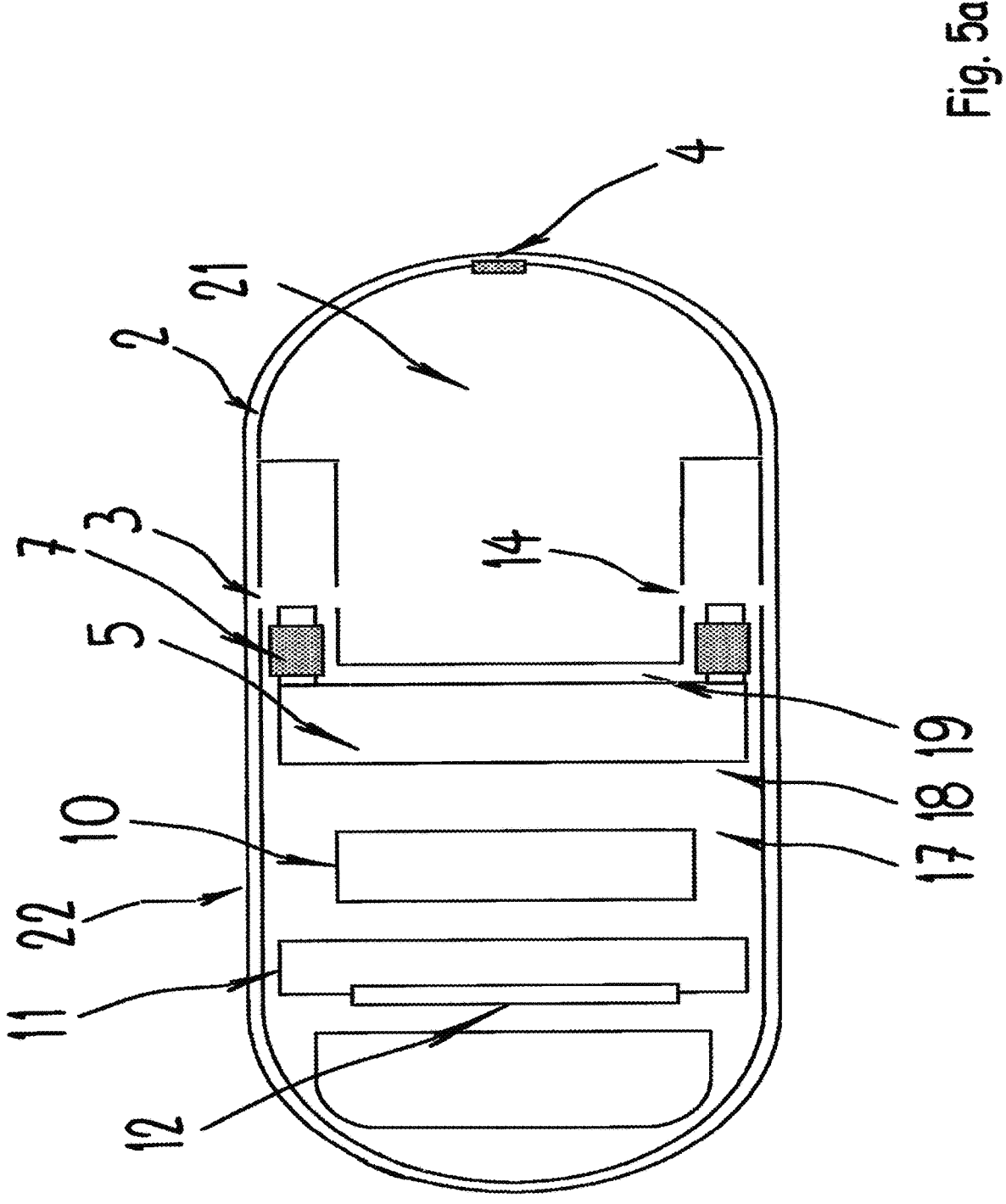
Figure 5B:
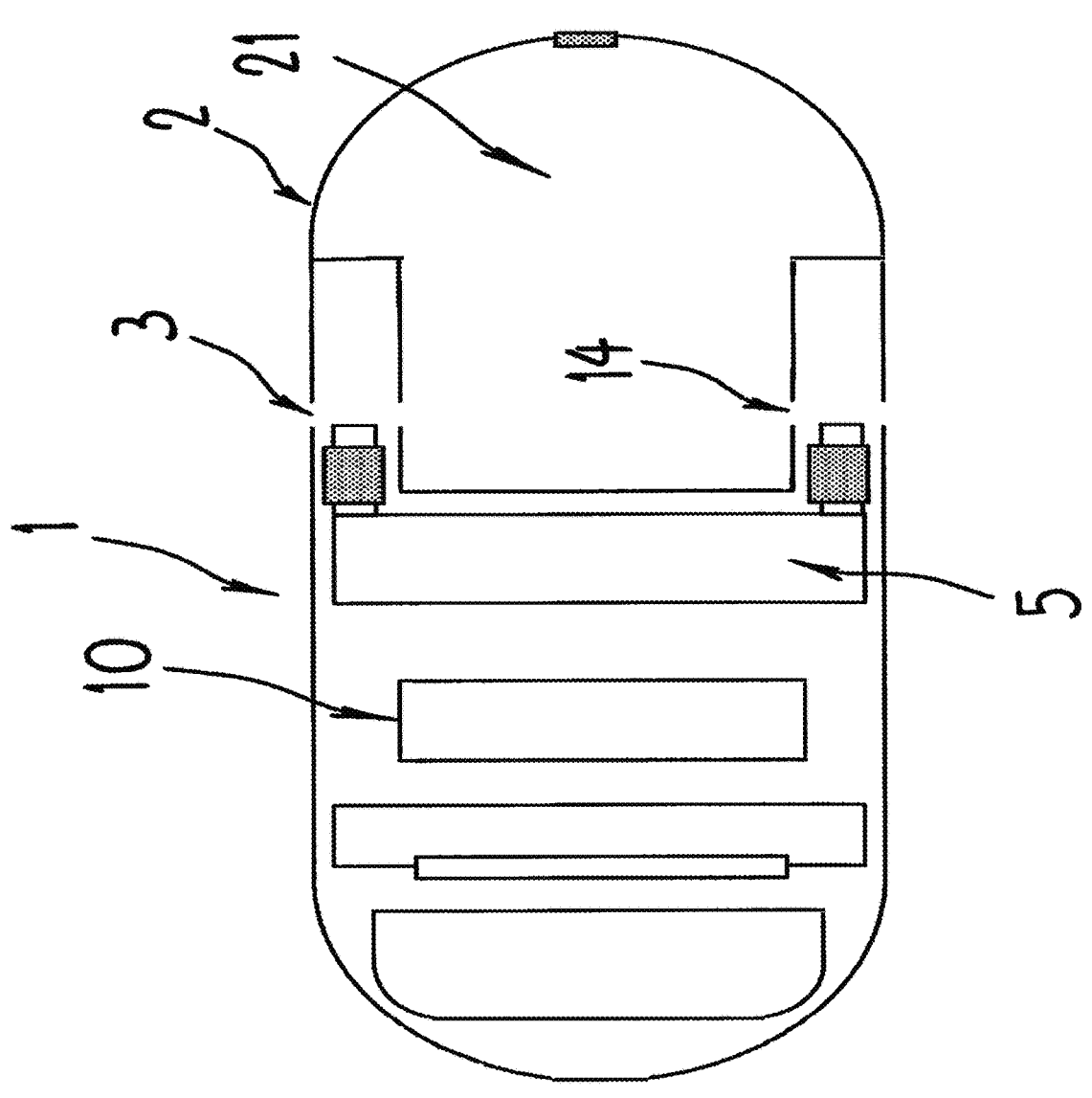
Figure 5C:
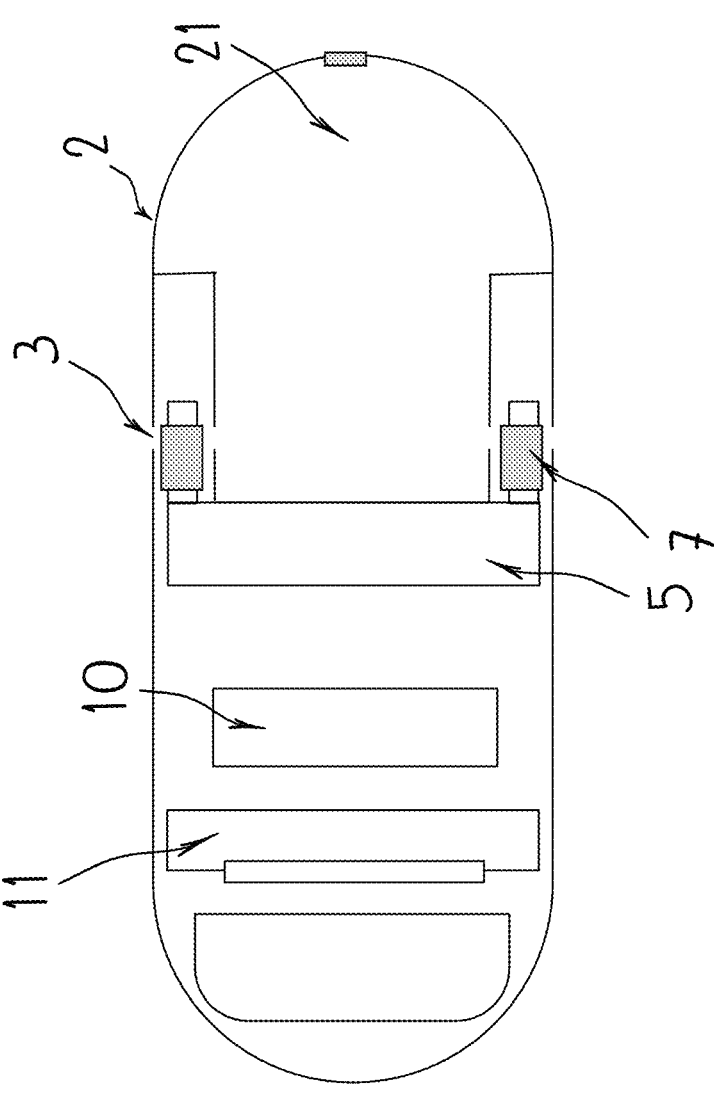

FIGS. 5a-5c show sectional views of a swallowable capsule 1 according to a second embodiment of the present invention. This capsule 1 has a modified piston 5 and a soluble seal 22 covering the outer shell 2 which dissolves after a given period of time in the GI tract of a subject. Components of the swallowable capsule 1 which are identical to those of the embodiment shown in FIGS. 2a-2c are provided with the same reference numbers.

In this embodiment of FIGS. 5a-c, the piston 5 comprises just one seal portion 7, but no piston opening 9. In an initial state, as illustrated in FIG. 5a, the piston 5 rests in an open position in which the passage between the shell openings 3 and the chamber openings 14 is unblocked. Fluid exterior to the shell 2 could principally enter into the sampling chamber 21, but this is prevented by the soluble seal 22 covering the outer shell 2 including the shell openings 3.

A given period of time after the capsule 1 has been swallowed, the soluble seal 22 has dissolved in the GI tract thereby unblocking the shell openings 3 and allowing fluid from exterior to the swallowable capsule 1 to enter into the sampling chamber 21. This state is shown in FIG. 5b.

Once a fluid sample has been collected and stored in the sampling chamber 21, the control unit 12 will drive the piston 5 to the closed position as shown in FIG. 5c.

In movement of the piston 5 may be time-controlled, i.e. the piston is automatically moved from the open to the closed position after a fixed period of time has lapsed after the capsule 1 has been swallowed. In another embodiment, the swallowable capsule 1 may comprise a fluid detector or any other kind of sensor which is apt to indicate that a fluid sample has entered into the sampling chamber 21. In this case, the gas drive unit is activated in response to determining that a fluid sample has entered into the fluid chamber 21.

In the closed position as shown in FIG. 5c, the piston closes a passage between the outer shell openings 2 and the sampling chamber 21 by means of it seal portion 7 thereby retaining the fluid sample within the chamber 21.

The soluble seal 22 may be made of an enteric material such as plant-derived HPMC or HPMCP.

Figure 6A:
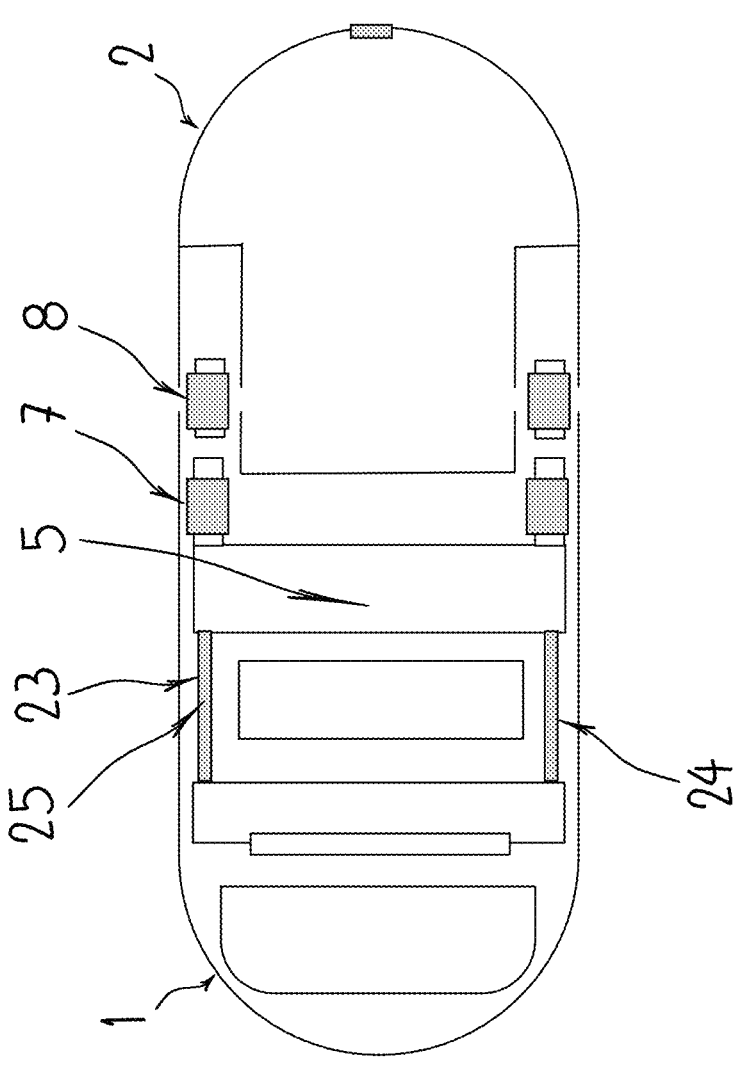
FIGS. 6a-6c are sectional views of a swallowable capsule similar to that of FIGS. 2a-2c with an additional position sensor for detecting the position of the piston.
Figure 6B:
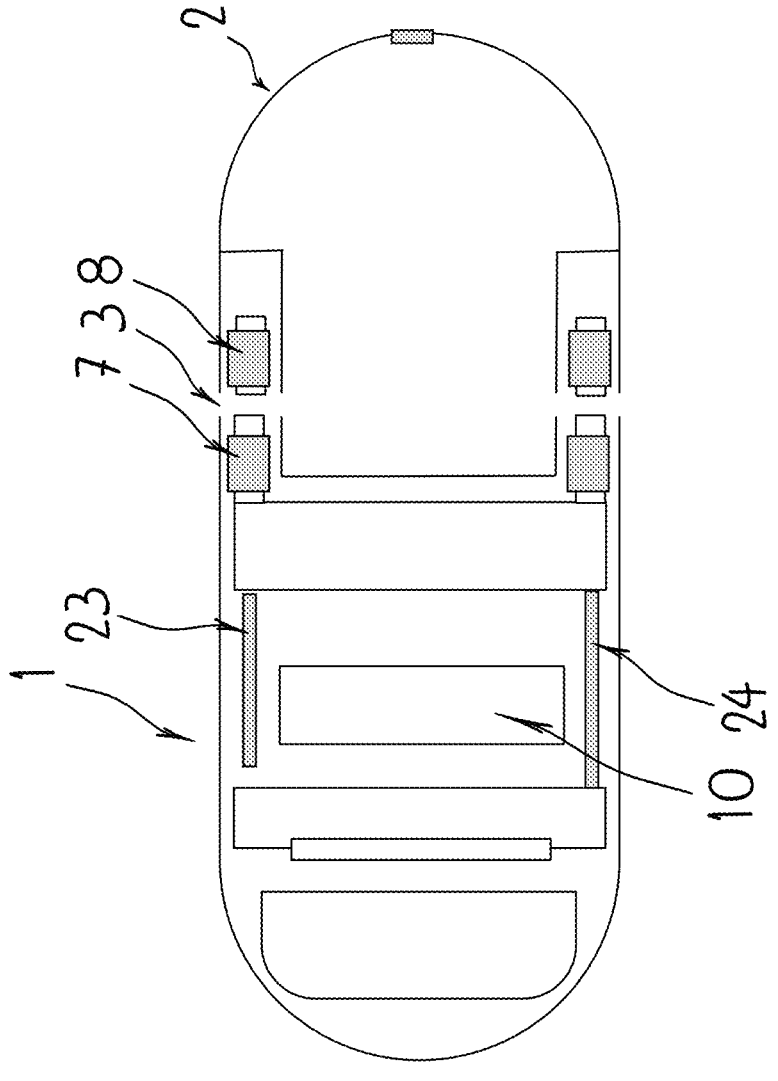
Figure 6C:
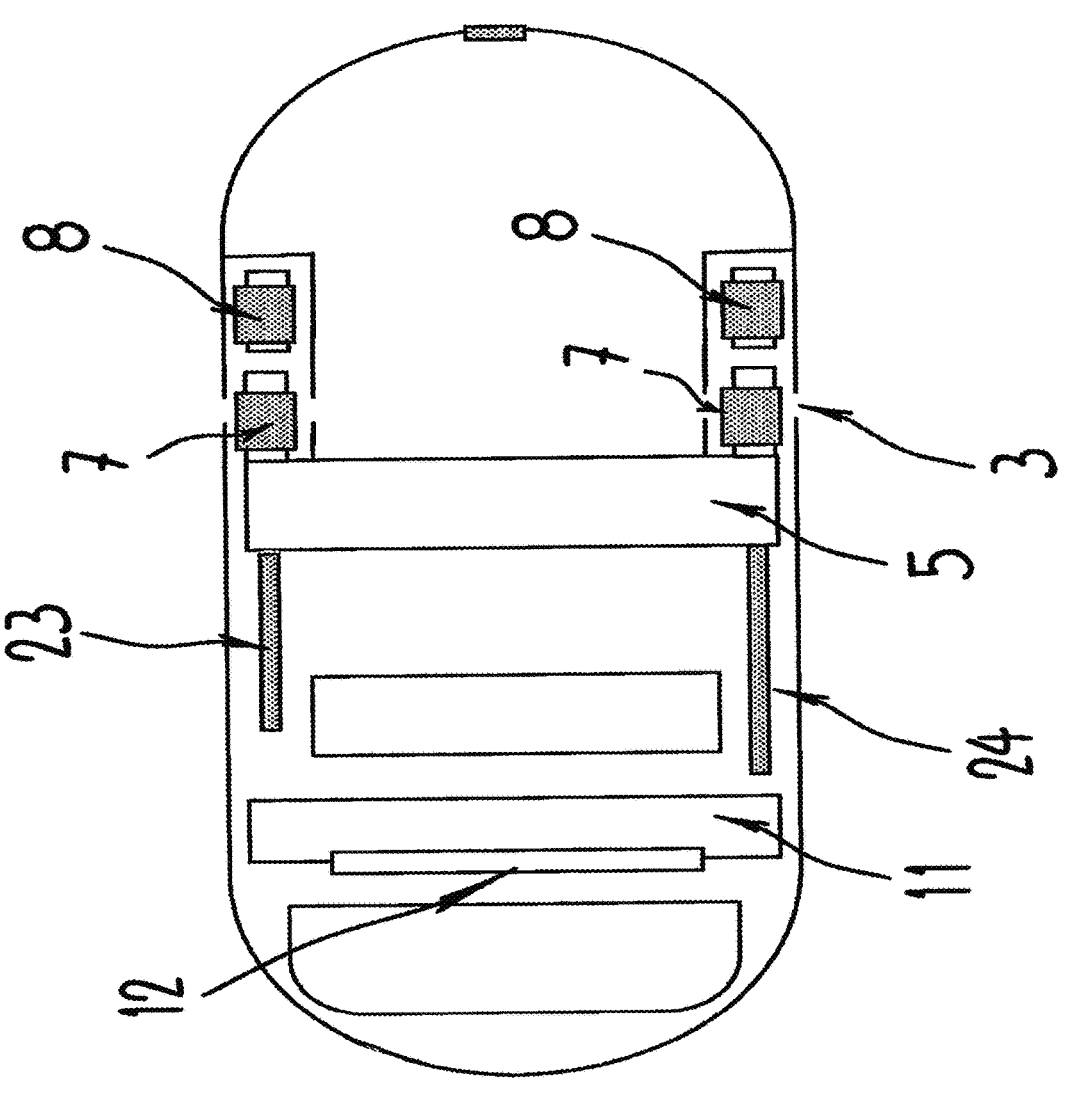

FIG. 6a-6c are sectional views of a swallowable capsule 1 similar to that of FIGS. 2a-2c. In this embodiment, the swallowable capsule 1 is equipped with an additional position sensor 25 for detecting the position of the piston 5.

Said position sensor 25 comprises two springs 23, 24 extending between the piston 5 and a PCB 11 providing an electrical contact. The springs are made of a conducive material such as metal and are arranged in a parallel relationship. One end of the springs 23, 24 is attached to the piston 5, the other end is free. The position sensor 25 may distinguish between two states per spring, namely a first state in which the free end of a spring 23, 24 is in contact with the PCB's 11 electrical contact, and a second state in which the free end is lift off from the PCB 11.

In an initial state of the piston 5 as shown in FIG. 6a, the springs 23, 24 are compressed between the piston and the contact surface. When the piston slides forward (here to the right), the springs 23, 24 extend until they reach their complete length. Since spring 23 is shorter than spring 24, it is spring 23 which will first lift off from the PCB'S 11 electrical contact surface, thereby indicating that the piston has reached the open position as shown in FIG. 6b. At this point, the control unit 12 controls the pressure generating device 10 so as to pause generating gas thereby stopping the piston 5 in the second position. After a preset period of time, the pressure generating device 10 increases pressure again in order to propel the piston to the third, closed position. Once the third position is reached, the long spring 24 will lift off from the PCB 11 thereby providing feedback that the piston 5 is in the third position and the sampling chamber 21 is resealed Finally, the swallowable capsule 1 described herein may comprise actuators, sensors, valves, chambers, logic devices, telemetry systems, microcontrollers or other devices and processors that may be configured using a combination of hardware, firmware, and software to carry out one or more of the methods described herein.

The invention claimed is:

1. A swallowable capsule configured to obtain fluid samples from the gastrointestinal (GI) tract of a subject comprising:

an outer shell enclosing an interior space;

the outer shell having a shell opening serving as an inlet port that allows a fluid sample to enter into the swallowable capsule;

a sampling chamber which may hold one or more samples obtained from the GI tract;

a piston which is moveably arranged in the interior space in a forward direction;

a pressure generating device operably disposed on one side of the piston, the pressure generating device configured to build up pressure on one side of the piston to propel the piston in the interior space at least from an open position allowing fluid from outside the swallowable capsule to enter into the swallowable capsule to a closed position, in which fluid exterior to the swallowable capsule is prevented from entering into the swallowable capsule;

the piston including a main body and an extension extending away from the main body, the extension providing at least a first seal portion and a piston opening defined therein, wherein the first seal portion is configured to close the shell opening in a first position of the piston thereby preventing fluid exterior to the swallowable capsule from entering into the capsule, wherein the piston opening is configured to align with the shell opening in a second position of the piston thereby allowing fluid from outside the swallowable capsule to enter into the capsule, the piston further including a second seal portion configured to close the shell opening in a third position of the piston thereby preventing fluid exterior to the swallowable capsule from entering into the capsule; and a control unit configured to control the pressure generating device so as to move the piston in the forward direction from the first position to the second position and then from the second position to the third position.

2. The swallowable capsule according to claim 1, wherein the shell opening is closed with a soluble seal which dissolves after a given period of time in the gastrointestinal (GI) tract of the subject thereby unblocking the shell opening.

3. The swallowable capsule according to claim 1, wherein the extension has the shape of a hollow cylinder or comprising one or several arms which extend in the forward direction on a low-pressure side of the piston.

4. The swallowable capsule according to claim 3, wherein the extension extends flush against and parallel to an interior wall of the shell.

5. The swallowable capsule according to claim 3, wherein the extension of the piston travels in a space between an interior wall of the shell and an exterior wall of the sampling chamber.

6. The swallowable capsule according to claim 5, wherein an outlet port is closed with a physical barrier which prevents fluid from the outside from entering into the swallowable capsule.

7. The swallowable capsule according to claim 1, wherein the sampling chamber has one or more chamber openings that allow a fluid sample to enter into the sampling chamber.

8. The swallowable capsule according to claim 7, wherein the piston is configured to open or close the shell openings as well as the one or more chamber openings at the same time, when the piston is in the open position or closed position.

9. The swallowable capsule according to claim 1, wherein a position sensor for detecting the position of the piston is arranged inside the shell, the position sensor comprising one or more springs extending between the piston and a contact surface providing an electrical contact.

10. The swallowable capsule according to claim 1, wherein the sampling chamber is arranged on a low-pressure side of the piston.

11. The swallowable capsule according to claim 1, wherein the outer shell has an outlet port which allows gas from the interior space on the low-pressure side of the piston to exit the swallowable capsule to the exterior.

12. The swallowable capsule according to claim 1, wherein the pressure generating device comprises a gas-generating cell that generates gas using a chemical process, or a pressure capsule filled with a pressurized gas released through a valve in order to build internal pressure within the shell and propel the piston.

13. The swallowable capsule according to claim 1, further comprising a locking mechanism operably engaged to the piston and configured to hold the piston in place in at least the second position.

* * * * *